United States Patent [19]

Costello et al.

[11] Patent Number: 5,554,153
[45] Date of Patent: Sep. 10, 1996

[54] LASER SKIN PERFORATOR

[75] Inventors: David J. Costello, Albuquerque, N.M.;
Aleksei Y. Dergatchev, Hoover, Ala.;
Warren E. Parkhurst, Houston, Tex.;
Valeri G. Polushkin; Sergey A. Kokhanovsky, both of Troitsk, U.S.S.R.

[73] Assignee: Cell Robotics, Inc., Albuquerque, N.M.

[21] Appl. No.: 297,295

[22] Filed: Aug. 29, 1994

[51] Int. Cl.$^6$ .................................................... A61B 17/36
[52] U.S. Cl. ................................ 606/9; 606/11; 606/16; 606/17
[58] Field of Search ..................... 606/9, 10, 11, 606/13, 16, 15, 17, 18; 433/29; 385/31

[56] References Cited

U.S. PATENT DOCUMENTS

| | | | |
|---|---|---|---|
| 3,500,240 | 3/1970 | Kessler | 331/94.5 |
| 3,530,397 | 9/1970 | Suzuki et al. | 331/94.5 |
| 3,538,453 | 11/1970 | Miller | 331/94.5 |
| 3,577,093 | 5/1971 | Simpson | 331/94.5 |
| 3,602,724 | 8/1971 | Smith | 307/88.3 |
| 3,615,312 | 10/1971 | Landry et al. | 65/4 |
| 3,639,855 | 2/1972 | Dillon, Jr. et al. | 331/94.5 |
| 3,646,471 | 2/1972 | DeMent | 331/94.5 |

(List continued on next page.)

FOREIGN PATENT DOCUMENTS

| | | |
|---|---|---|
| 1928665 | of 1970 | Germany . |
| 2011322 | of 1971 | Germany . |
| 59-1048232 | 4/1991 | Japan . |
| 1026596 | of 1966 | United Kingdom . |
| 93/10279 | of 1992 | WIPO . |

OTHER PUBLICATIONS

"New In Laser Medicine And Surgery," USSR State Committee On Science And Technology, USSR Ministry of Health, Moscow, 1990 (w/ translation).

(List continued on next page.)

*Primary Examiner*—Michael H. Thaler
*Assistant Examiner*—Sonya Harris-Ogugua
*Attorney, Agent, or Firm*—Guy McClung

[57] ABSTRACT

A laser perforator is disclosed for perforating skin with a perforation to permit blood under a surface of the skin to flow out, the perforator in one embodiment having a laser light source for producing an output laser beam, and a mode distribution means for intercepting the output laser beam to control distribution of laser energy of the output laser beam across the perforation of the skin. A laser perforator is disclosed for perforating skin with a perforation to permit blood under a surface of the skin to flow out, the perforator in one embodiment having a laser light source for producing an output laser beam having an energy level between about 0.1 to about 2.0 Joules, and a mode distribution means for controlling mode distribution of the output laser beam across the perforation of the skin, the mode distribution means including a cylindrical laser rod to produce ring mode distribution of the output laser beam, the cylindrical laser rod having a 90 degree annular corner reflector to produce a ring mode distribution of the output laser beam, a doughnut lens for focusing the output laser beam, the perforation ranging in diameter between about 0.1 to about 2.0 millimeters, in depth between about 0.5 to about 4.0 millimeters, and ranging in width between about 0.05 to about 0.2 millimeters. A method is also disclosed for perforating skin for blood sampling, the method including producing a laser beam from a laser, the beam having an energy level and a plurality of energy modes, distributing the energy modes of the beam by mode distribution means for evenly distributing the energy modes, producing an output beam with an evenly distributed mode distribution, and directing the output beam to the skin and producing a perforation through the skin through which the blood flows. A laser perforator is disclosed for perforating skin with a perforation to permit blood under a surface of the skin to flow out, the perforator having a laser light source for producing an output laser beam, and a mode distribution means for producing a ring shaped profile of the output laser beam.

9 Claims, 5 Drawing Sheets

U.S. PATENT DOCUMENTS

| | | | |
|---|---|---|---|
| 3,654,482 | 4/1972 | Massey | 307/88.3 |
| 3,660,779 | 5/1972 | Cuff et al. | 334/94.5 |
| 3,675,156 | 7/1972 | Danielmeyer | 331/94.5 |
| 3,680,000 | 7/1972 | Chesler et al. | 331/94.5 |
| 4,575,854 | 3/1986 | Martin | 372/75 |
| 4,641,912 | 2/1987 | Goldenberg | 350/96.1 |
| 4,648,892 | 3/1987 | Kittrell et al. | 65/4.21 |
| 4,712,537 | 12/1987 | Pender | 128/9 |
| 4,731,795 | 3/1988 | Clark et al. | 372/107 |
| 4,740,047 | 4/1988 | Abe et al. | 350/96.15 |
| 4,797,896 | 1/1989 | Kane | 372/94 |
| 4,800,886 | 1/1989 | Nestor | 128/634 |
| 4,822,335 | 4/1989 | Kawai et al. | 604/20 |
| 4,848,323 | 7/1989 | Marijnissen et al. | 128/6 |
| 4,912,713 | 3/1990 | Langhans | 372/66 |
| 4,949,728 | 8/1990 | Brook | 128/760 |
| 4,955,377 | 10/1990 | Lennox et al. | 128/401 |
| 4,984,885 | 1/1991 | Ortiz, Jr. | 356/153 |
| 4,994,060 | 2/1991 | Rink et al. | 606/28 |
| 5,019,075 | 5/1991 | Spears et al. | 606/7 |
| 5,037,172 | 8/1991 | Hekman et al. | 385/31 |
| 5,048,044 | 10/1991 | Ireland | 372/66 |
| 5,057,099 | 10/1991 | Rink | 606/12 |
| 5,074,861 | 12/1991 | Schneider et al. | 606/17 |
| 5,077,745 | 12/1991 | Aoshima et al. | 372/18 |
| 5,102,410 | 4/1992 | Dressel | 606/15 |
| 5,165,418 | 11/1992 | Tankovich | 128/760 |
| 5,169,395 | 12/1992 | Narciso, Jr. | 606/7 |
| 5,253,312 | 10/1993 | Payne et al. | 385/31 |
| 5,255,275 | 10/1993 | Motegi | 372/29 |
| 5,290,273 | 3/1994 | Tan | 606/9 |
| 5,292,320 | 3/1994 | Brown et al. | 606/15 |
| 5,298,018 | 3/1994 | Narciso, Jr. | 604/21 |
| 5,298,026 | 3/1994 | Chang | 606/15 |
| 5,304,170 | 3/1994 | Greene | 606/9 |
| 5,312,395 | 5/1994 | Tan et al. | 606/9 |
| 5,319,528 | 6/1994 | Raven | 362/32 |
| 5,388,987 | 2/1995 | Badoz et al. | 433/29 |
| 5,468,239 | 11/1995 | Tanner et al. | 606/15 |

OTHER PUBLICATIONS

"Int'l Conference New In Laser Medicine," Moscow, 1991 (w/ translation).

"Annual Accounting By The USSR Academy of Sciences," 1991 (w/ translation of 10th paragraph).

"Ultraviolet Excimer Laser Ablation: The Effect of Wavelength and Repetition Rate On In Vivo Guinea Pig Skin," Journal of Investigative Dermatology, 1987.

"Ultraviolet–Laser Ablation Of Skin," Arch Dermetol, 1985.

"Pulsed Photo Thermal Radiometry of AbsorptionYag:Er and $CO_2$ Laser Radiation In Biological Tissues," Sov. Journal Quantum Electron. 1989.

U.S. Official Gazette entries for U.S. Patents 5,124,997; 5,124,998; 5,124,999; 5,125,000; 5,125,001; 23 Jun. 1992, pp. 2642, 2643.

"Attention! New Laser Perforator NTEC–303," Mammology, Jan. 1993 (w/translation).

"A Needle Without A Needle, A Finger Stick Without Sticking A Finger...," Tekhnika–Molodezh; Engineering for Youth, Dec. 1993 (w/translation).

LASER SKIN PERFORATOR

BACKGROUND OF THE INVENTION

1. Field of the Invention

This invention relates to lasers and laser systems, and, in one aspect to a laser-device for producing a hole in skin through which blood may be withdrawn. In one particular aspect this invention relates to modifying the output profile of a laser beam to produce improved skin perforators.

2. Description or Related Art

Capillary blood sampling is a process for obtaining blood samples from the sub-dermal capillary beds of patients. A common method is to produce a small wound in the patient's skin using a sharp needle or small blade, called a blood lancet. Lancets are commonly used once and discarded. The lancet procedure produces a sharp, blood infected waste product which represents a risk to patients and health care workers, and which must be disposed of under carefully controlled conditions. In addition, the use of disposable blood lancets requires the health care providing organization to maintain a large inventory of disposable lancets. Certain lancet designs include an exposed point which produce significant fear and apprehension in patients who anticipated a painful experience. Although modem designs have attempted to eliminate such apprehension, reduction of patient discomfort would significantly increase the usefulness of new capillary sampling techniques.

Lasers typically have a light source for optical excitation, an active laser material, and a set of reflecting mirrors. Most solid state lasers have a design with a rod of laser crystal or glass material optically pumped by a high intensity lamp or set of LED arrays, with mirrors placed a distance from, or in contact with, or coated onto, the surfaces of the laser rod. One mirror has either a hole or a reduced reflectance relative to the other. Light is injected from the lamp or LED array into the laser material initiating the discharge of photons from dopants in the rod. These photons travel between the two mirrors producing light amplification. The amplified laser beam escapes the system through the hole or area of reduced reflectance. As an active medium various lasant materials are used to produce different wavelengths of laser light. These materials include, but are not limited to, rare-earth-doped oxide and fluoride laser crystals and glasses, e.g. yttrium-aluminum-garnet (YAG). Such crystals and glasses will be doped with impurities to fix the resultant wavelength of the laser. These traditional laser designs have precise mirrored surfaces. The reflective surfaces are usually made by coating the surfaces with several thin layers of dielectric material. If separate mirrors are used, they are placed precisely with respect to the optical axis of the laser rod and with respect to each other. The reflective mirror surfaces can be also produced by coating them onto the polished faces of a laser crystal.

Modal distribution is a property of projected light. A projection mode can be characterized by an angular direction vector in which light beams may travel with respect to some normal angle. The normal angle is defined usually as 0 degrees with respect to the optical axis of a system. The modal distribution of a system can be characterized by a set of angular vectors in which light travels upon output from the system. A low order distribution is one in which most of the energy in a light beam travels parallel or near to parallel with the optical axis. Most commonly available laser devices are designed to have a low order distribution of modes; i.e., most devices are designed so that light energy travels only in the 0th order mode (parallel to the normal vector) or within a small set of angular vectors surrounding the normal vector. A higher order distribution is one in which energy light travels at greater angles with respect to the optical axis.

Laser perforators are disclosed in U.S. Pat. No. 5,165,418, in Japanese patent 4,314,428, and in PCT patent application US93/10279. Certain lasers of the type described in these publications will typically exhibit a low order distribution of modes with radiant energy concentrated toward the center of the beam and, thus, the holes, or wounds, produced are relatively deep and penetrating with respect to the thickness of the skin. Such wounds are the shape of a champagne glass with a broad entrance wound and a longer slender stem. Blood is found to be available from the upper bowl portion of the wound, but little blood escapes from the lower portion, or stem, of the wound. A variety of low-order mode distribution lasers have been developed and are used in medical applications, such as eye surgery, tissue necrosis, and sensor probes.

There has long been a need to produce capillary blood samples without the production of hazardous waste products. There has long been a need to eliminate the use of disposable implements for performing such procedures while reducing worker exposure to infectious disease. There has long been a need to reduce patient discomfort and pain associated with capillary blood collection.

SUMMARY OF THE PRESENT INVENTION

The present invention provides evenly distributed laser energy across a wound site, producing a more closely regulated wound with respect to diameter and depth. Obtaining access to capillary blood with this system provides a less painful sensation to the patient and better control of the wound profile with respect to previously disclosed laser-based skin perforators. Evenly distributed energy across a greater set of modal vectors produces a more controlled wound profile. In certain embodiments of the present invention, control over the mode distribution of the laser beam is achieved by the following: a) optimization of the geometry of laser active element; b) optimization of the laser resonator geometry; c) use of external spatial filters; or d) use of optical fibers and waveguides. Projecting the laser beam with high mode distribution on the skin according to the present invention produces an upper wound profile with a relatively broad bowl portion without production of the lower, less useful, portion of a wound. Such laser perforator systems also produce less pain among subjects. Incorporation of mode distribution allows greater control of a wound profile and collection of blood, while producing less pain in subjects. Any suitable laser may be used according to the present invention; including, but not limited to, solid-state lasers, gas lasers, dye lasers, diode lasers, and diode-pumped solid-state lasers. In one aspect the output laser beam has an energy level ranging between about 0.1 to about 2 Joules and in one particular aspect the energy level is about 1 Joule. In certain aspects a pulsed laser beam is used with a pulse width ranging between 50 and 500 microseconds.

According to the present invention, a laser perforator system is designed to control the mode distribution of output laser beam or has apparatus for the mode distribution of a laser beam, including but not limited to, a hollow waveguide, a solid optical fiber waveguide, spatial filters, specific laser active element geometries, and specific laser active element materials.

Laser light projected into the interior of a hollow waveguide (such as a capillary tube, miniature metal tube, or optical fiber) is reflected from the walls of the waveguide producing a modal distribution which expands along the length of the waveguide. Optical fiber waveguides generate expanded modal distributions of light beams. Optical fibers are designed so that light reflecting from the walls is effectively retained within the fiber. It is possible to launch light into the fiber in such a way as to generate higher order modes. Bends in the optical fiber may be used to generate or reject specific portions of the modal distribution, especially higher order modes, allowing control of the output distribution.

Spatial filters reduce the amount of energy traveling in particular cross sectional areas of a laser beam. Usually, low order modes are reduced by filtering the center of the beam. The use of spatial filtering, however, reduces the overall energy of a beam, reducing the energy efficiency of a system.

It is common knowledge that one design feature of laser devices is the modal distribution of the output beam. In virtually all cases of laser design the designer tries to produce a very low order distribution of modes, including designs of value in other fields which produce a single mode output. It is not obvious that one should reverse the objectives of common laser design practices in order to produce a more useful laser perforator. Modal distribution of laser output may be manipulated by changes in the geometry of the laser active element. For example the laser element described in U.S. patent application Ser. No. 08/204,560, entitled LASER, filed on Mar. 1, 1994 and co-owned with the present invention (incorporated herein by reference for all purposes, full copy appended hereto) describes a solid state laser crystal geometry which produces an output with a multi-mode distribution. In general, the inclusion of reflective surfaces into the laser cavity which are not orthogonal to the optical axis of the laser system design, will produce increased order of modal distribution.

It has been found that certain laser materials naturally produce higher order mode distribution. For example, a laser constructed with erbium-doped Yttrium Scandium Aluminum Garnet (YSAG) active element has a higher order distribution than the same laser built with erbium-doped YAG (YAG:Er).

In certain embodiments the present invention discloses devices as discussed above with apparatus for producing a laser output beam with a ring profile; in one aspect a hollow cylindrical rod accomplishes this. A system according to this invention includes such apparatus and a laser light source.

The present invention recognizes and addresses the previously mentioned problems and long-felt needs and provides a solution to those problems and a satisfactory meeting of those needs in its various possible embodiments and equivalents thereof. To one of skill in this art who has the benefits of this invention's realizations, teachings, disclosures, and suggestions, other purposes and advantages will be appreciated from the following description of preferred embodiments, given for the purpose of disclosure, when taken in conjunction with the accompanying drawings. The detail in these descriptions is not intended to thwart this patent's object to claim this invention no matter how others may later disguise it by variations in form or additions of further improvements.

In one aspect the present invention discloses a laser perforator for perforating skin with a perforation to permit blood under a surface of the skin to flow out, the perforator having a laser light source for producing an output laser beam, and a mode distribution means for intercepting the output laser beam to control distribution of laser energy of the output laser beam across the perforation of the skin. In another aspect such a laser perforator has a laser light source for producing an output laser beam having an energy level between about 0.1 to about 2.0 Joules, a mode distribution means for controlling mode distribution of the output laser beam across the perforation of the skin, the mode distribution means including a cylindrical laser rod to produce ring mode distribution of the output laser beam, the cylindrical laser rod having a 90 degree annular corner reflector to produce a ring mode distribution of the output laser beam, a doughnut lens for focusing the output laser beam, with the perforation ranging in diameter between about 0.1 to about 2.0 millimeters, in depth between about 0.5 to about 4.0 millimeters, and ranging in width between about 0.05 to about 0.2 millimeters. The present invention teaches a method for perforating skin for blood sampling to produce a perforation to permit blood under a surface of the skin to flow out, the method including, comprising, or consisting of producing a laser beam from a laser, the beam having an energy level and a plurality of energy modes, distributing the energy modes of the beam by mode distribution means for evenly distributing the energy modes, producing an output beam with an evenly distributed mode distribution, and directing the output beam to the skin and producing a perforation through the skin through which the blood flows. In another embodiment the present invention discloses a laser perforator for perforating skin with a perforation to permit blood under a surface of the skin to flow out, the perforator having a laser light source for producing an output laser beam, and a mode distribution means for producing a ring shaped profile of the output laser beam. In one such perforator the ring has a diameter ranging between about 0.1 to about 2.0 millimeters and a slit perforation is produced ranging in depth between about 0.5 to about 4.0 millimeters and ranging in width between about 0.05 to about 0.2 millimeters.

A more particular description of embodiments of the invention briefly summarized above may be had by references to the embodiments which are shown in the drawings which form a part of this specification. These drawings illustrate certain preferred embodiments and are not to be used to improperly limit the scope of the invention which may have other equally effective or legally equivalent embodiments.

DESCRIPTION OF EMBODIMENTS PREFERRED AT THE TIME OF FILING FOR THIS PATENT

Figure 1A:
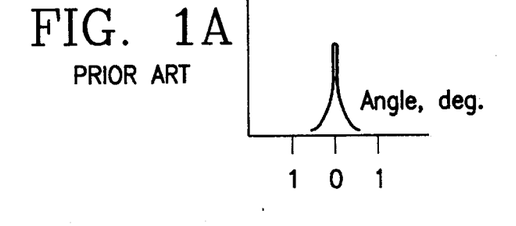
FIG. 1A is a graph demonstrating low order mode distribution for a prior art laser perforator.
Figure 1B:
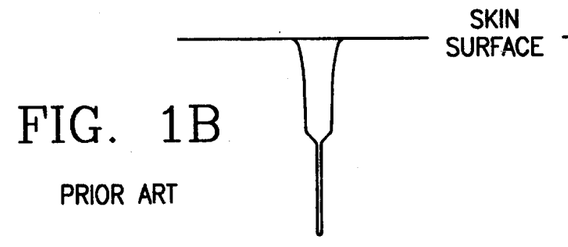
FIG. 1B is a schematic representation of a dermal wound produced by a laser with a mode distribution as in FIG. 1A.

Referring to FIG. 1, FIG. 1 A shows a graphical representation of a beam profile such as commonly available from laser system designs which do not employ the use of a mode distribution mechanism, as described in the prior art. The vertical axis shows the normalized intensity of the laser and the horizontal axis indicates location in the beam with respect to the axial optical center of the beam ("O"). FIG. 1B shows a schematic representation of the lateral view of holes produced in skin by such lasers as determined by experiments conducted under the direction of the inventors. Normalized intensity shows the relationship of beam intensity versus distance from the beam's axial optical center (O) in arbitrary units. A maximum value for intensity versus distance is 1.

Figure 2A:
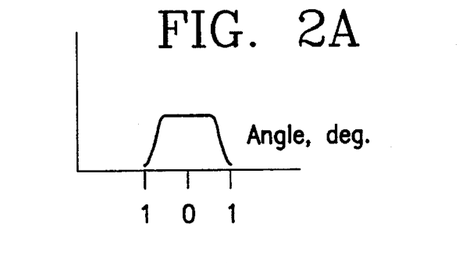
FIG. 2A is a graph of high order mode distribution for a laser according to the present invention and FIG. 2B shows schematically a dermal wound produced by such a laser.
Figure 2B:
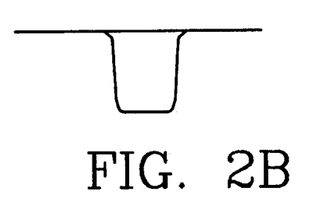

FIG. 2A shows a representation of a beam profile achieved when using a mode distribution mechanism according to the present invention. Again the vertical axis shows normalized intensity. FIG. 2A shows a representation of the lateral cross section of holes in skin obtained when using such a system. The lower portion "stem" portion of the hole is noticeably missing. In addition the relatively broad profile of the hole intersects a greater number of subdermal capillaries, producing more blood availability from wounds of this type, while minimizing the volume of tissue ablated and the sensation of pain to the subject.

Figure 3A:
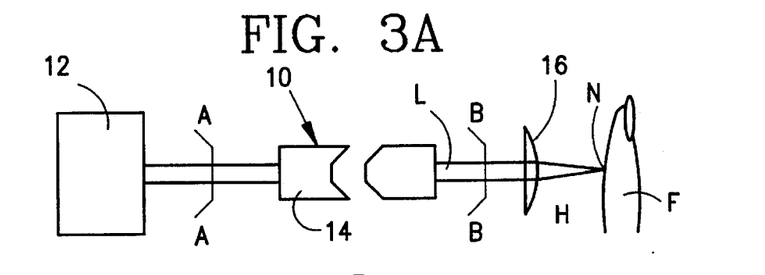
FIG. 3A is a schematic view of a laser-based skin perforation system according to the present invention.

Referring now to FIG. 3A, a system 10 according to the present invention has a light generator 1 (e.g. a solid state laser based on YAG:Er, or GGG:Er, or YAP:Er, or other laser with fundamental output wavelength suitable for perforating the skin) and a mode distribution apparatus 4 [e.g. but not limited to a hollow waveguide; a solid optical fiber; or a spatial filter] which produce a laser light beam L which is focused by lens 16 onto a finger F of a patient to produce a hole H which perforates the sub-dermal capillary bed of the finger and through which the patient's blood may flow for exterior collection.

Figure 3B:
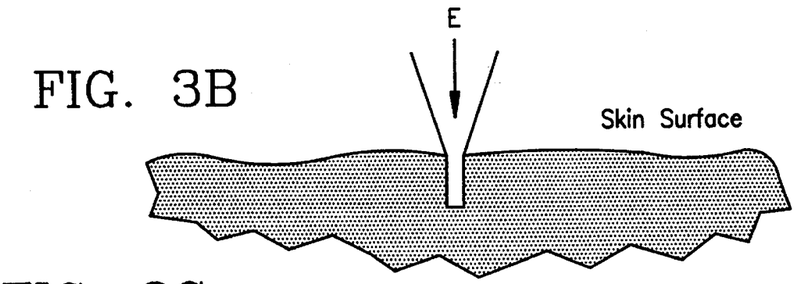
FIG. 3B is a detail view of the wound-site produced by the perforator system of FIG. 3A.
Figure 3C:
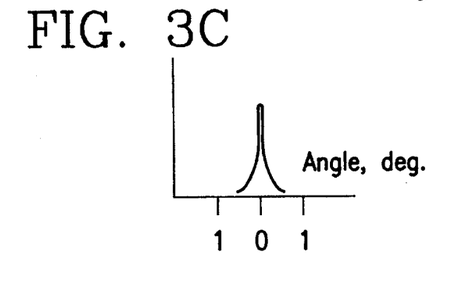
FIG. 3C shows the modal distributions at plane A—A of FIG. 3A.
Figure 3D:
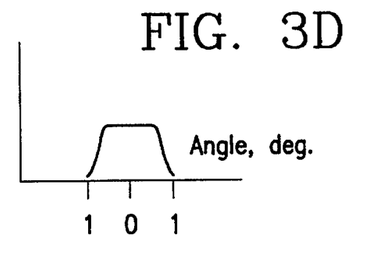
FIG. 3D shows the modal distribution at plane B—B of FIG. 3A.

FIG. 3B shows a schematic representation of a wound in skin produced with the system of FIG. 3A. FIG. 3C shows a representation of the beam distribution profile before the mode distributor at plane A—A of FIG. 3A and FIG. 3D shows the distribution after the mode distributor at plane B—B of FIG. 3A. The vertical axes in FIGS. 3C and 3D are normalized intensity and the horizontal axis represents the optical axis of the beam (center at O).

Figure 4A:
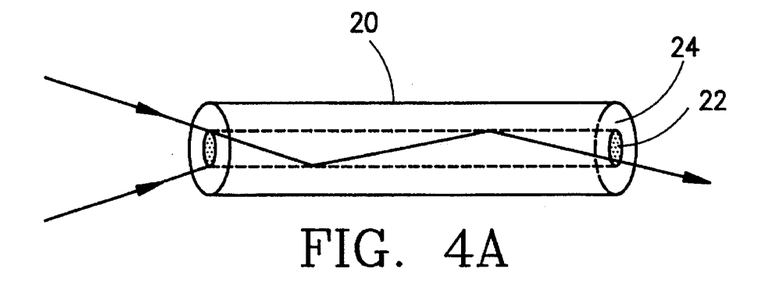
FIG. 4A is a side schematic view of a mode distributor for use according to the present invention.
Figure 4B:
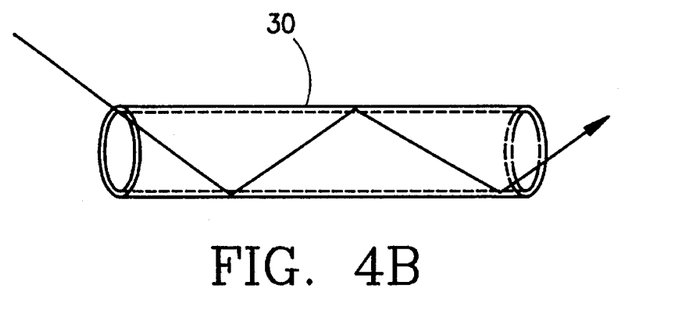
FIG. 4B is a side schematic view of a mode distributor for use according to the present invention.
Figure 4C:
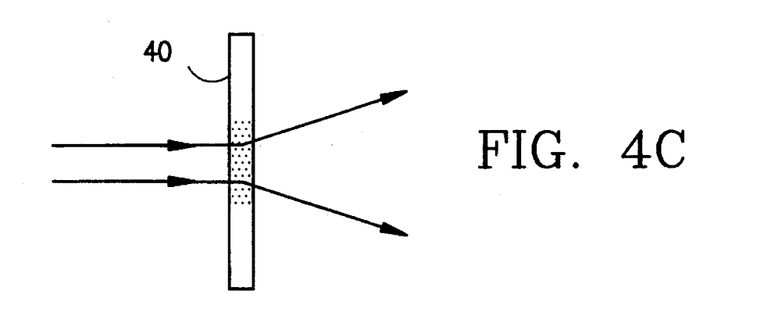
FIG. 4C is a side schematic view of a mode distributor for use according to the present invention.

FIG. 4A shows mode distributor as an optical fiber 20 with a core 22 and cladding 24. FIG. 4B shows a mode distributor as a light waveguide 30. FIG. 4C shows mode distributor as a spatial filter 40. In each case multiple reflections of the laser beam (indicated by arrow) incident to the mode distributor result in a higher order mode distribution at the output of the mode distribution mechanism. (Inputs shown on left, outputs to the right in the Figs.)

Figure 5A:
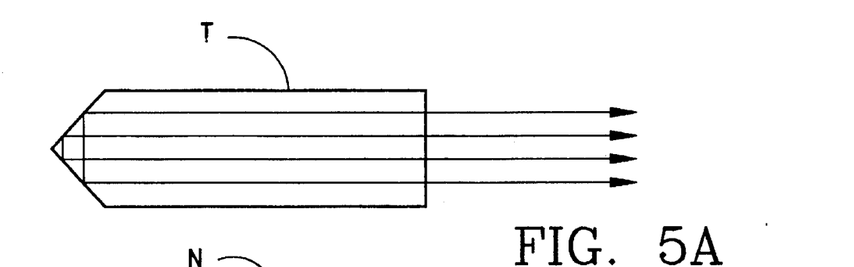
FIG. 5A is a side view of a laser active element for use according to the present invention.
Figure 5B:
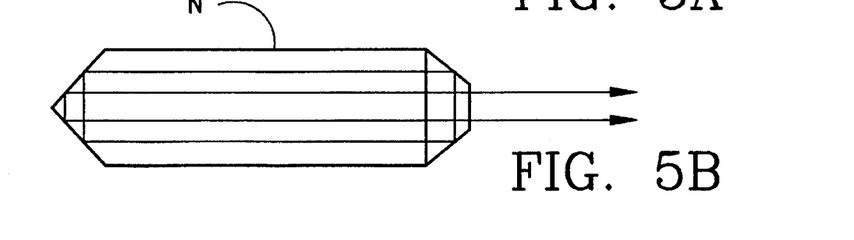
FIG. 5B is a side view of a laser active element for use according to the present invention.

In certain embodiments the light generator 12 includes an active laser element (e.g. but not limited to those described in pending U.S. application Ser. No. 08/204,560) as the element T shown in FIG. 5A. Also, angular reflection surfaces (e.g. as described in but not limited to those of U.S. application Ser. No. 08/204,560) as the element N shown in FIG. 5B may be used in the light generator 12 to increase the modal distribution of the output beam (arrows indicate light paths and reflected light paths).

Figure 6A:
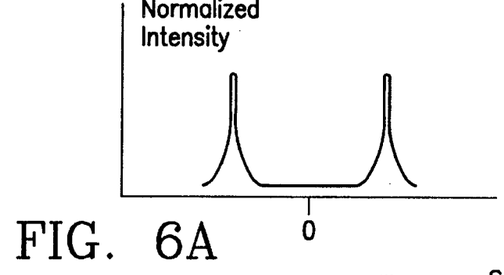
FIG. 6A is a graph of a "ring" mode distribution for a laser system according to the present invention.
Figure 6B:
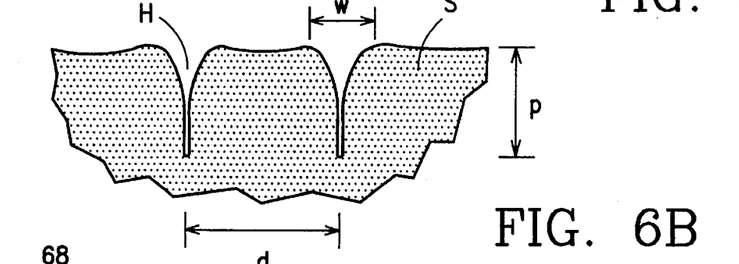
FIG. 6B shows schematically a lateral view of a dermal wound produced by such a laser system.
Figure 6C:
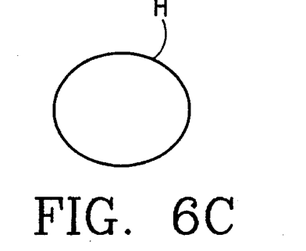
FIG. 6C shows a top-view of the ring shaped wound produced by such a laser system.
Figures 7A, 7B:
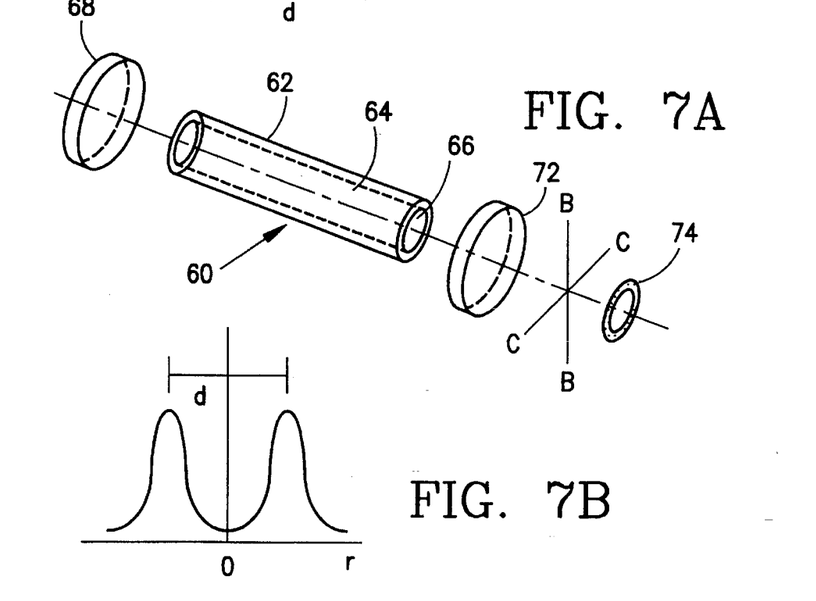
FIG. 7A shows the optical system to produce a laser beam with ring mode distribution according to the present invention.
FIG. 7B and 7C show graphs of laser beam energy distribution across axes B—B and C—C of FIG. 7A.

FIG. 6A illustrates a mode distribution for a laser beam produced with apparatus according to the present invention as shown in FIG. 7A. A sub-dermal hole H in skin S produced by such a beam is shown in FIGS. 6B and 6C. In such an embodiment the modal distribution has a "ring" shape of the output beam so that a circular slit (hole H) is produced in the skin rather than a hole as produced by previously described embodiments. Such slits have been found to be less painful than wider holes. In one particular embodiment a circular slit about 0.05 millimeters wide ("w" in FIG. 6B) is produced with a diameter ("d") of about 0.75 mm, a depth ("p") of about 2 mm, and an outer circumference of about 2.4 mm by a YAG:Er laser operated at about a 1 Joule energy level for about 200 microseconds.

It is within the scope of this invention to provide mode distribution apparatus to produce a ring shaped output beam. FIG. 7A illustrates a solid state laser system 60 for producing a laser beam with "ring" shape according to the present invention. The system 60 has a hollow cylindrical body 64 made, e.g., from YAG:Er, YAP:Er, GGG:Er, YSAG:Er etc. with a central hollow longitudinal channel 66 along its length. Light reflected by a back mirror 68 and a partially reflective mirror 72 is amplified in a hollow cylindrical active laser element 62 producing a "ring" shape laser beam.

Figure 7C:
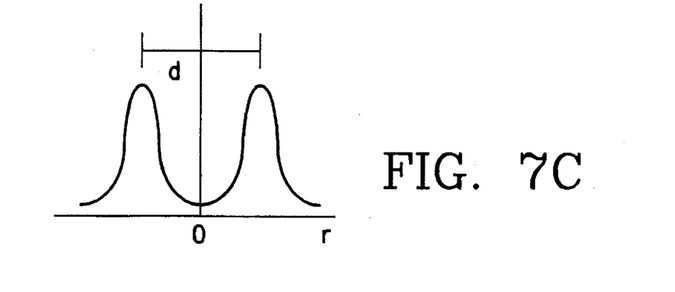

FIG. 7B is a graph of laser beam energy distribution at axis B—B of FIG. 7A: and FIG. 7C is a graph of laser beam energy distribution at axis C—C of FIG. 7A. "O" in each figure indicates the device's central optical axis. It is within the scope of this invention that the laser beam energy distribution output profile be asymmetrical with respect to the optical axis of the device and that the energy mode distributions not be identical.

Figure 8A:
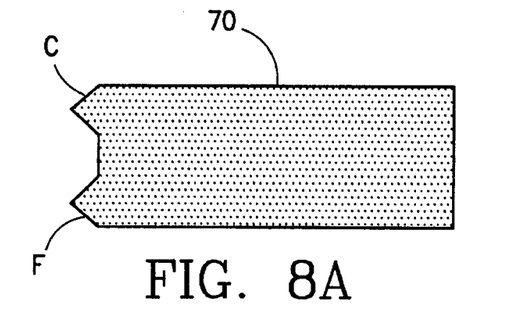
FIG. 8A is a side view of a laser active element for use according to the present invention.
Figure 8B:
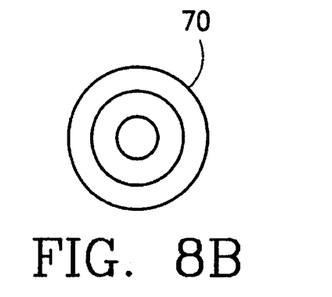
FIG. 8B is an end view of the element of FIG. 8A.
Figure 8C:
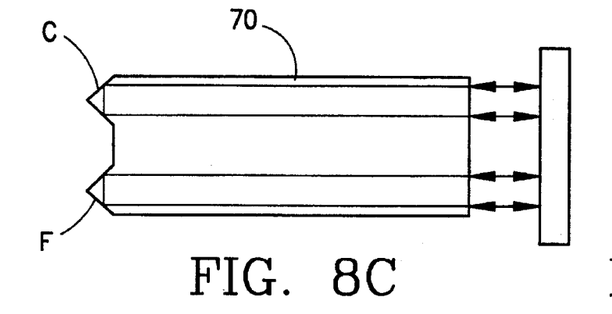
FIG. 8C is a schematic representation of the element of FIG. 8A showing the paths of laser light rays.
Figure 8D:
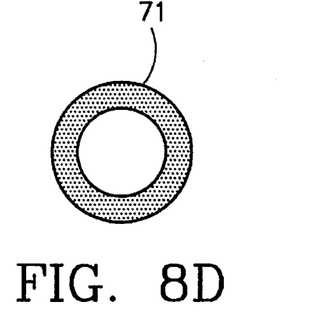
FIG. 8D shows the cross-sectional ring shape of the laser output beam.
Figure 8E:
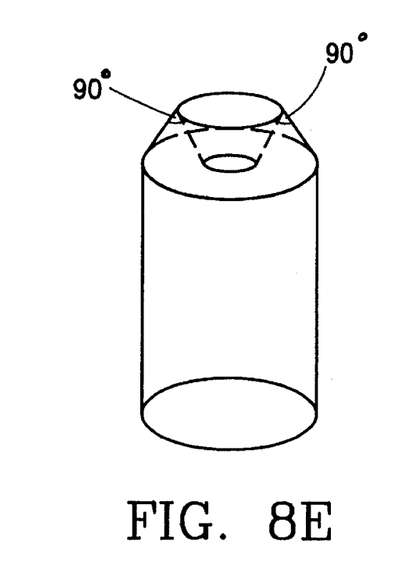
FIG. 8E is a perspective view of the element of FIG. 8A.

FIG. 8A and 8C show an active element 70 for achieving a laser beam with a "ring" shape. The active element 70 is not a hollow cylinder but a cylindrical element with one face made with a cone C which forms a 90 degree reflector (see FIG. 8C) within which a further conical surface F has been ground with an apex diametrically opposed to the cone C such that the conical surface forms the circular reflective surface at that end of the element. The resulting reflective surface can also be described as the upper surface of a solid which would be generated by the 360 degree rotation of a fight triangle having two equal sides with the bottom side being less in length or equal to the radius of the laser rod. This annular 90 degree reflector plays a two-fold role: 1) it works like a back mirror, and 2) it determines the back boundary of the resonation cavity of the laser rod. In this design the central pan of the rod R is not used to produce a laser beam. Only cylindrical layer limited by the annular corner reflectors produces a laser beam, a beam with a ring shape.

Figure 9A:
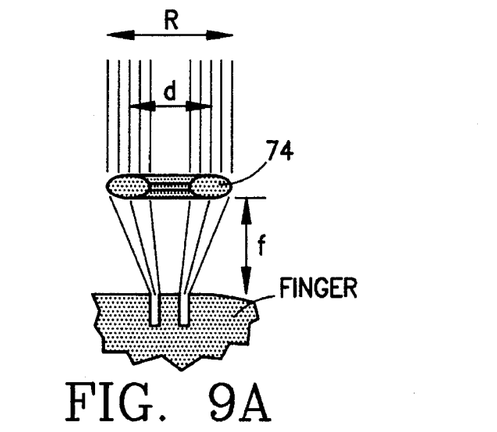
FIG. 9A is a schematic view showing use of a doughnut lens according to the present invention.
Figure 9B:
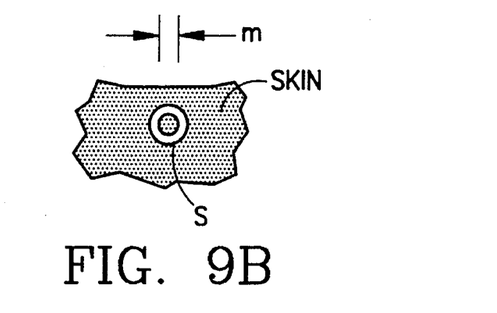
FIG. 9B is a top view of the wound shown in FIG. 9A.

The lens 74 (FIG. 7A, 9A) is used to focus the laser beam with the ring shape to decrease the diameter and the thickness of the ring slit in order to make a circle cut in patient's finger. The lens 74 has a doughnut shape. The diameter d of the lens 74 is determined by the diameter R of the ring shape laser beam (See FIG. 9A). The focal distance f of the lens 74 is chosen preferably to achieve a desired diameter m for the circle slit S on the skin. (See also FIG. 9B.)

Lasers emitting a ring shaped beam may also be used with mode distributions mechanisms as described above to further control the laser system output profile.

Figure 10A:
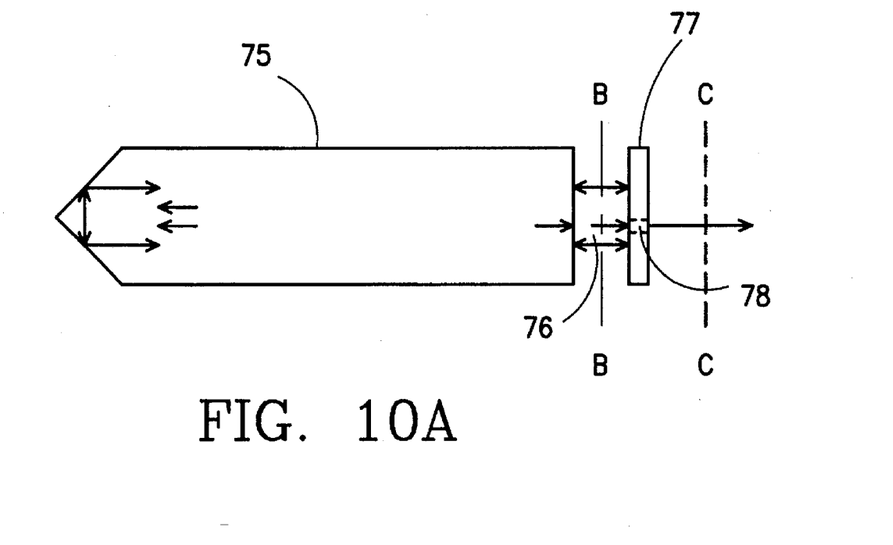
FIG. 10A is a schematic view of a system according to the present invention.
Figure 10B:
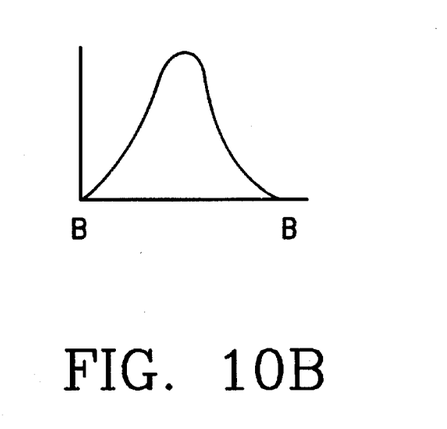
FIG. 10B is a graph of the mode distribution of the beam energy levels of the beam of the device of FIG. A along axis B—B of FIG. 10A.
Figure 10C:
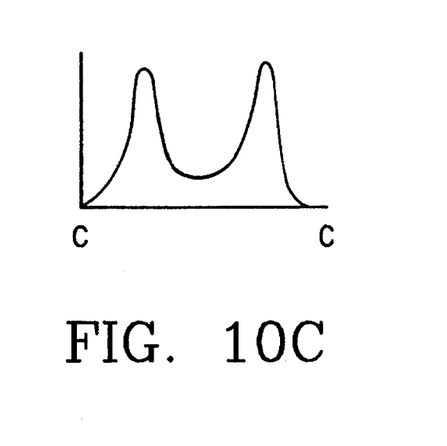
FIG. 10C is a graph of the mode distribution of the beam along axis C—C of FIG. 10A.

FIG. 10A shows another system according to the present invention for producing a ring-shaped laser output profile. In this system a laser rod 75 produces an output beam 76 which is directed toward a mirror 77. The mirror 77 has a hole 78 in it which is preferably centered slightly off the optical axis of the laser system. In this case light impinging on the hole is selected for high-order modes. The output profile of the beam passing through the hole has a ring-shaped profile and produces a ring-shaped wound in skin. FIG. 10B shows the beam's mode at axis B—B of FIG. 10A and FIG. 10C shows the beam's mode distribution at the axis C—C of FIG. 10A. It is within the scope of this invention to provide a hole in the mirror not on the optical axis of the invention at any desired distance from the optical axis.

Pending application Ser. No. 08/204,560 is incorporated fully herein by reference for all purposes and a copy thereof is submitted with the application for this patent.

In certain preferred embodiments of each of the previously described systems and lasers, the laser output beam is pulsed, preferably with a pulse width between 50 and 500 microseconds.

In conclusion, therefore, it is seen that the present invention and the embodiments disclosed herein and those covered by the appended claims are well adapted to carry out the objectives and obtain the ends set forth. Certain changes can be made in the subject matter without departing from the spirit and the scope of this invention. It is realized that changes are possible within the scope of this invention and it is further intended that each element or step recited in any of the following claims is to be understood as referring to all equivalent elements or steps. The following claims are intended to cover the Invention as broadly as legally possible in whatever form it may be utilized.

What is claimed is:

1. A laser perforator for perforating skin with a perforation to permit blood under a surface of the skin to flow out, the perforator comprising a laser light source for producing an output laser beam, and a mode distribution means for intercepting the output laser beam to control distribution of laser energy of the output laser beam across the perforation of the skin the mode distribution means is a cylindrical rod having a 90 degree annular corner reflector having a conical surface with an apex diametrically opposed to the cone so that the conical surface forms a circular reflective surface at the end of said means.

2. The laser perforator of claim 1 further comprising, the mode distribution means for producing ring mode distribution of an output laser beam.

3. The laser perforator of claim 2 further comprising a doughnut lens for focusing the output laser beam.

4. The laser perforator of claim 1 wherein the energy level of the output laser beam ranges between about 0.1 to about 2.0 Joules incident on the skin.

5. The laser perforator of claim 1 wherein the perforation ranges in diameter between about 0.1 to about 2.0 millimeters and the perforation ranges in depth between about 0.5 to about 4.0 millimeters.

6. The laser perforator of claim 2 wherein the ring has a diameter ranging between about 0.1 to about 2.0 millimeters and a slit perforation is produced ranging in depth between about 0.5 to about 4.0 millimeters and ranging in width between about 0.05 to about 0.2 millimeters.

7. The laser perforator of claim 1 wherein the output laser beam has an energy level of about 1.0 Joules.

8. The laser perforator of claim 7 wherein the output laser beam is pulsed at between 50 and 500 microseconds.

9. A laser perforator for perforating skin with a perforation to permit blood under a surface of the skin to flow out, the perforator comprising a laser light source for producing an output laser beam having an energy level between about 0.1 to about 2.0 Joules, and a mode distribution means for controlling mode distribution of the output laser beam across the perforation of the skin, the mode distribution means including a cylindrical laser rod to produce ring mode distribution of the output laser beam, the cylindrical laser rod having a 90 degree annular corner reflector having a conical surface with an apex diametrically opposed to the cone so that the conical surface forms a circular reflective surface at the end of said means to produce a ring mode distribution of the output laser beam, a doughnut lens for focusing the output laser beam, the perforation ranging in diameter between about 0.1 to about 2.0 millimeters, in depth between about 0.5 to about 4.0 millimeters, and ranging in width between about 0.05 to about 0.2 millimeters.

* * * * *